United States Patent [19]

Magnusson et al.

[11] 4,455,381

[45] Jun. 19, 1984

[54] IMMUNOASSAY OF PROTEINS

[75] Inventors: Carl-Gustaf M. Magnusson, Brussels; Daniel Collet-Cassart, Limal; Pierre L. Masson, Brussels, all of Belgium

[73] Assignee: International Institute of Cellular and Molecular Pathology, Belgium

[21] Appl. No.: 319,023

[22] Filed: Nov. 6, 1981

[30] Foreign Application Priority Data

Nov. 7, 1980 [GB] United Kingdom ............... 8035794

[51] Int. Cl.³ .................................... G01N 33/68
[52] U.S. Cl. ............................... 436/543; 436/512; 436/513; 436/518; 436/528; 436/534; 436/825
[58] Field of Search .................. 424/1; 23/230 B; 436/512, 518, 536, 543, 547, 174, 175, 177, 178, 825

[56] References Cited
PUBLICATIONS

Bluard–Deconink et al., Biochemical Journal, vol. 171, pp. 321–327, (1978).
Bluard–Deconink et al., J. Clinical Endocrinology Metabolism, vol. 42, pp. 189ff, (1976).

Primary Examiner—Benjamin R. Padgett
Assistant Examiner—M. Moskowitz
Attorney, Agent, or Firm—S. P. Tedesco

[57] ABSTRACT

In the immunoassay of a particular protein in a biological fluid, there is frequently interference in the assay by other proteins present in the fluid, e.g. by complement factors or antibodies in human serum. The interference so caused can be avoided by subjecting the fluid to protein-digestion, using for example an enzyme such as pepsin, as a result of which the particular protein of interest, or a fragment thereof, can be assayed without interference by the other proteins. Also, radioallergosorbent tests for particular IgE antibodies can be improved in sensitivity and accuracy, by subjecting the absorbed IgE to enzymic digestion, and then assaying a fragment thereof.

19 Claims, 1 Drawing Figure

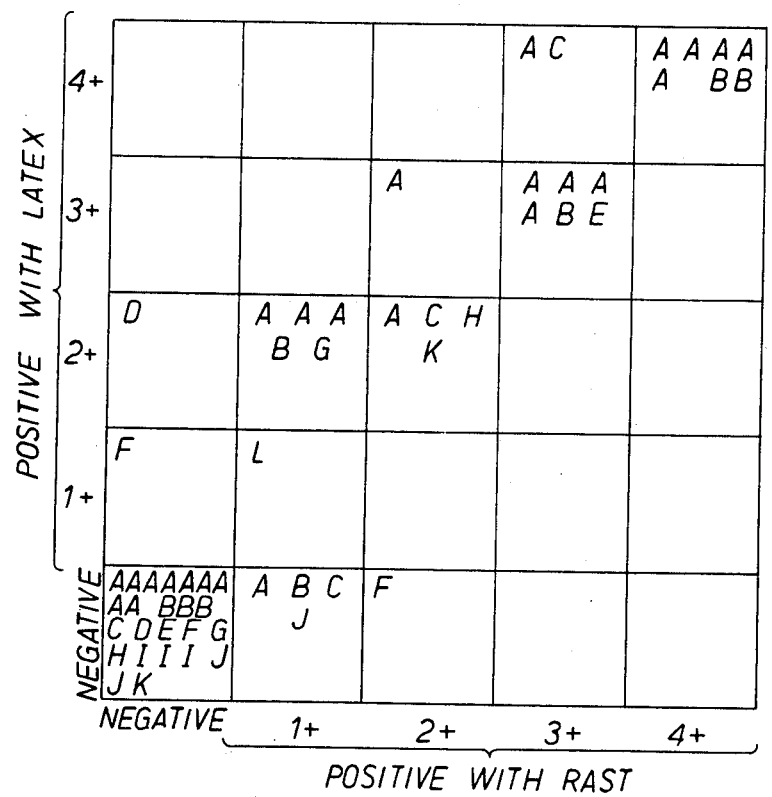

|  | NEGATIVE | 1+ | 2+ | 3+ | 4+ |
|---|---|---|---|---|---|
| 4+ | | | | A C | A A A A<br>A  B B |
| 3+ | | | A | A A A<br>A B E | |
| 2+ | D | A A A<br>  B G | A C H<br>  K | | |
| 1+ | F | L | | | |
| NEGATIVE | A A A A A A A<br>A A  B B B<br>C D E F G<br>H I I J<br>J K | A  B C<br>  J | F | | |

POSITIVE WITH LATEX (vertical axis) / POSITIVE WITH RAST (horizontal axis)

IMMUNOASSAY OF PROTEINS

This invention relates to the immunoassay of proteins.

In the immunoassay of serum and other biological fluids for a protein of interest, there is commonly interference in the assay by other substances present in the fluid. For example, complement factor and rheumatoid factor, both of which are endogenous to human blood serum, tend to interfere by reacting with antibodies used in the assay. Further, other proteins present in the serum tend to interfere through non-specific protein-protein interactions. There have been various proposals made for avoiding these interferences. For example, interference by complement factor or rheumatoid factor can be overcome by using, in the assay, the F(ab')$_2$ fragments of antibody instead of whole antibody. The F(ab')$_2$ fragments are immunospecific to the protein under assay but do not react with complement or rheumatoid factor. This technique is described in our U.K. patent specification No. 2013688 to which reference should be made for further details. The effect of non-specific protein-protein interactions can be substantially reduced by the use of chaotropic agents as described in our published European specification No. 0038181 to which reference should be made for further details.

Interference from serum proteins is also a problem in the immunoassay of non-protein antigens (which term includes haptens). For example, not only can serum proteins interfere in the assay reaction, but also the antigen under assay may be bound to serum proteins and have first to be released therefrom before the assay can be effected. However, interferences of this sort may be overcome by first digesting the serum proteins using an enzyme such as pepsin (the non-protein antigen being unaffected). The enzyme is then inactivated or destroyed prior to the assay. This procedure is described for example, in J. Clin. Endocrinol. Metab. 42,189 (1976), and it is suggested there that this techique may be of broad application in the assay of non-peptide ligands in serum (but not, of course, peptide ligands which would be destroyed by the enzyme).

The enzymatic digestion of proteins is, of course, well known. It results in the breaking up of the protein molecule into smaller fragments. It is a technique used, for example, in the determination of the amino acid sequence in proteins. The mechanism of such cleavage and hence the precise constitution of the fragments, various with the enzyme used and the conditions (e.g. time, temperature and pH) under which the digestion is effected. It has been reported that, in some instances, enzymatic digestion of a biologically active protein can result in the formation of a fragment which retains some biological or immunological activity (see, for example, J-M Bluard-Deconink et al, Biochem J. 171 (1978), 321-327; U. J. Leuvis et al, "Growth Hormone and Related Peptides", Excerpta Medica, Amsterdam 1976, p. 64; U. J. Leuvis et al, Biochem. Biophys. Res. Commun., 67, 617 (1975)). So far as enzymic digestion has been suggested for destruction of serum proteins in the assay of non-protein antigens, however, the digestion is effected so as to completely neutralise the protein interferents, i.e. to break them down so that they no longer interfere in the assay of the non-protein antigen.

We have now found that the advantages obtainable by enzymic digestion of interfering proteins in the immunoassay of non-protein antigens can be obtained, together with other advantages, in the immunoassay of protein antigens. In particular, we have found that, very surprisingly, liquids containing two or more proteins, only one of which is to be assayed, can be subjected to protein digestion and the selected protein of interest thereafter assayed without interference from the other proteins.

BRIEF DESCRIPTION OF THE DRAWINGS

FIG. 1 is a graph comparing results obtained with the pepsin elution procedure as compared with those of the RAST method.

In one aspect, the invention provides a method of immunoassay of a selected protein in a liquid sample also containing one or more other non-selected proteins, which comprises reducing or avoiding interference from said other proteins by mixing with the liquid sample a protein-digesting reagent, and allowing protein digestion to occur under conditions such that the said selected protein provides, in the resulting mixture, an antigenic determinant which is distinctive only thereof in the said mixture; and thereafter assaying the said antigenic determinant and determining therefrom the amount of said selected protein present in the liquid sample.

In the method of the invention, the liquid sample, which will usually be of biological origin, e.g. serum, is treated with a reagent which causes protein digestion. This reagent can be a chemical such as cyanogen bromide, dimethyl sulphoxide/hydrobromic acid, dithiothreitol or other known such reagents, but we prefer to use an enzyme. The preferred protease is pepsin, but other proteases can be used such as, for example, papain and trypsin. It will be understood that different enzymes break down proteins in different ways, i.e. at different points along the polypeptide chains, and at different rates, and some preliminary routine trials may be desirable to determine the best enzyme and conditions (e.g. pH, time, ionic strength, temperature) in any particular case. The invention is hereinafter described mainly with reference to enzymic digestion but it is to be understood that chemical digestion (though less preferred) can be used.

The liquid under assay, containing the selected protein of interest and one or more other proteins (hereinafter called "interfering proteins"), is mixed with a protease, e.g. pepsin. In the case of serum, the "interfering proteins" may for example be complement factors, rheumatoid factor (IgM and IgG), albumin, pre-albumin, and various antibodies. The enzymic digestion is generally effected so as to break down the "interfering proteins" at least to an extent such that, in the subsequent assay, they do not interfere. Generally, each of the interfering proteins will be broken down into two or more fragments. The selected protein may also be fragmented, or it may in certain cases be substantially unaffected by the enzyme. For the purposes of the present invention, it does not matter in principle whether the protein of interest becomes fragmented or not: the most important point is that the liquid sample is modified by the digestion so that the "interfering proteins" can no longer interfere in the assay. It will usually be the case that the "interfering proteins" will be fragmented by the digestion step. It is possible, however, according to the invention, that the interfering proteins are substantially unaffected by the digestion but the selected protein is fragmented. Subsequent assay of the fragmented protein (as described hereinafter) may then be effected without interference by the "interfering proteins".

The exact mechanism of digestion is unimportant provided that, as a result, the selected protein can be assayed without interference from the other, non-selected proteins. Most usually, and preferably, the non-selected proteins will be broken down in the digestion, and the selected protein will also usually be fragmented (but not always). The mechanism depends, of course, on the nature of the proteins and of the enzyme, and also on the conditions under which the digestion is effected.

When, as a result of the digestion, the "interfering proteins" are fragmented but the selected protein is substantially unaffected, it can be assayed using the antigenic determinant of the whole selected protein. One selected protein which can be so assayed by the method of the invention is thyroid stimulating hormone (TSH) in human serum. If an enzymic digestion step is effected using pepsin, the TSH is little affected and, after digestion, can be assayed as for whole TSH. Interfering proteins in the serum are, however, fragmented and as such do not thereafter interfere in the assay.

In the most usual case, both the interfering proteins and the selected protein are digested to form fragments. According to a feature of the present invention, the digestion is effected under conditions such that the selected protein forms a fragment which is antigenically distinctive, in the mixture, only of said selected protein. The fragment is then assayed.

To identify an antigenically distinctive fragment, a sample of the protein of interest is enzymatically digested, and the protein or polypeptide fragments so formed are separated by chromatography. The major fragments are then each injected into an antiserum-producing animal, for example, a rabbit. Normally it will be found that one fragment will produce a high titre or avidity antiserum and this fragment will be the antigenically distinctive fragment of choice. It is noteworthy that this fragment in the original whole protein molecule may not have exhibited (or been responsible for) any antigenic activity at all since it may have been so hidden in the molecule that it was inactive due to steric hindrance. The antisera formed in this way against the antigenically distinctive fragment are preferably used in the assay of the fragment in the digested serum.

An important feature of a preferred method of the invention is that, upon controlled digestion of a mixture of the selected and other proteins, fragments may be obtained at least one of which will be antigenically distinctive of the particular selected protein only and can thus be assayed to indicate the presence and amount of that protein in the original sample.

Whilst the invention is of particular utility in the assay of immunoglobulin E (IgE), as is more fully described hereafter, it is also useful with other immunoglobulins and other proteins such as TSH (as previously described), follicle stimulating hormone (FSH) and human growth hormone (HGH), for example. These proteins are all relatively large molecules (e.g. over 50,000 molecular weight). Relatively small proteins, such as insulin and angiotensin I and II, are more difficult to assay by the method of the present invention because any fragments produced on digestion of the liquid sample tend to be rather small for subsequent assay. In any particular case, the suitability of such small proteins for assay by the method of the invention can be determined by simple preliminary trial. The method of the invention is applicable not only to the assay of whole proteins, but also to the assay of protein fragments.

In the method of the invention, the antigenic determinant which, in the digestion mixture, is distinctive of the selective protein, is assayed. As stated previously, this determinant may be that of the whole protein or that of a distinctive fragment formed therefrom. There are many different methods of assay which can be used. We prefer to use a latex particle assay (described more fully hereafter) but, whilst this is in many cases highly advantageous, it is not essential. Examples of other methods include the following:

(a) the use of an antibody to the antigenic determinant (or other selective binding substance), which is immobilised, for example on the wall of a tube;
(b) radioimmunoassay utilising a radio-labelled substance and antibody;
(c) immunoradiometric assay using a radio-labelled antibody;
(d) other known assays involving a label, e.g. fluorimetric, enzymatic or chemiluminescent labels.

These techniques, and others, are well known in the art and will not be further described herein.

In the assay step of the invention, in which the antigenic determinant distinctive of the selected protein is measured, we prefer to react the said determinant with an antibody. Preferably, the antibody has been raised specifically against the said determinant. Thus, for example, when the selected protein has fragmented, we prefer to raise antibody against the distinctive fragment and to use this antibody to assay the fragment. Whole antibody can be used or, alternatively, Fab fragments such as F(ab')2 fragments can be used in the absence of F(c) fragments and of the whole antibody (see our U.K. specification No. 2013688). Where herein we refer to "the F(ab) region of an antibody" we mean either the F(ab) region of a whole intact antibody, or F(ab) fragments (e.g. F(ab')2) which have been separated from the F(c) part of an antibody. Hereinafter, references to the use of antibody include references to the use of whole antibody and of F(ab) fragments of antibody.

The preferred assay techniques for the present invention are latex particle agglutination techniques. There are several such techniques, all of which are or are becoming well known in the art. Of these, the following are preferred:

(a) the digestion mixture containing the antigenic determinant of interest is mixed with latex particles carrying antibody against the said antigenic determinant e.g. against the distinctive fragment. Agglutination occurs to an extent dependent on the quantity of that antigenic determinant and the extent of agglutination is measured either directly or, more preferably, by counting the unagglutinated latex particles;

(b) the digestion mixture containing the antigenic determinant is mixed with antibody (against the determinant) to form "antibody:antigen complexes". The complexes are mixed with latex particles having a coating of IgG and with a limited amount of agglutinator such as RF or mouse serum agglutinator (MAG). The particles and the complexes compete for the limited quantity of agglutinator, and the extent of agglutination is measured to provide an assay of the amount of the antigenic determinant in the original sample;

(c) the digestion mixture containing the antigenic determinant is mixed with latex particles bearing the same antigenic determinant, and a limited amount of antibody thereto. The particles and the free antigenic determinant compete for the limited quantity of antibody. An agglutinator, such as RF or MAG, is then added which causes agglutination of those particles to which antibody has become bound. The extent of agglutination is measured to provide an assay of the amount of antigenic determinant in the original sample;

(d) the digestion mixture containing the antigenic determinant is mixed with latex particles bearing the same antigenic determinant, and with smaller latex particles carrying antibody thereto. The free antigenic determinant inhibits agglutination between the two different particles, and the extent of agglutination is measured to provide an assay of the amount of the antigenic determinant in the original sample.

In all these techniques, use is made of standard results obtained by performing the test on samples containing known amounts of the antigenic determinant, i.e. of the whole selected protein or of the antigenically distinctive fragment thereof derived under controlled conditions from samples of known amounts of particular proteins. The general techniques are fully described in Technicon Instruments Corporation literature on PACIA (particle counting immunoassay) and also in, for example, Cambiaso et al, 1977 J. Immunol. Methods 23,29, to which reference should be made for further details. In most of the above assays, we prefer to use, in place of whole antibody, the F(ab) fragments thereof, e.g. the F(ab')$_2$ fragments, as described in our U.K. specification No. 2013688.

As is well known, IgE is the immunoglobulin involved in allergic responses. The presence in human sera of IgE antibodies to a particular allergen indicates an allergic response to that allergen, and the quantity of such antibodies gives some measure of the intensity of the allergic reaction. It is important to be able quantitatively to measure particular IgE's, for example to establish whether a patient is exhibiting an allergic response to a drug. It can also be important to be able to measure the total amount of IgE (i.e. the sum total of all the IgE antibodies of various specificities) present in a serum sample. However, the total amount of IgE present in human sera is very small, and any one particular IgE antibody will be present in even tinier amounts. Very sensitive test techniques are therefore necessary and protein interferences of the type described above assume major importance.

The main test currently used to establish the presence and amount of a particular IgE in serum is the so-called RAST test (radioallergosorbent test). In this test, the serum or blood sample is placed in contact with an absorbent disc bearing the appropriate allergen. The IgE antibodies (if any) against the allergen become bound to the allergen on the disc. The disc is then washed and the bound IgE is then measured using $^{125}$I-labelled IgE antibodies. Each such test takes about 24 hours and is relatively labour intensive and expensive in its use of radio-labelled IgE.

A modified RAST test has recently been described by Gleich et al (J. Allergy Clin. Immunol., Vol. 65, No. 1, pp 20-28—January 1980) which is called a mini-RAST test. In this test, the IgE under assay is selectively taken up by solid-phase allergen. It is then assayed using radio-labelled antisera raised against F(c) fragments of the IgE under assay. The fragments are made using papin to cleave the IgE. It is to be noted that this procedure is conventional except that the antisera used have not been raised against whole IgE but against the specific F(c) fragment thereof produced by papain (which cleaves IgE at one position only).

In a preferred embodiment of the present invention, the RAST test is modified in that the disc is contacted with a protease to digest the bound IgE. A fragment is produced which is antigenically distinctive of the IgE, and the fragment is then quantitatively assayed. This digestion technique greatly improves the accuracy and reproducibility of the recovery from the disc, thus increasing the sensitivity and reliability of the test procedure.

Thus, according to a further aspect of the present invention, there is provided a method of assaying a selected protein in a biological fluid sample also containing one or more other non-selected proteins, whereby interference in the assay from said other proteins is avoided and the specificity and accuracy of the assay improved, which method comprises:

(a) contacting said sample with an inert solid support material bearing a reagent which selectively binds only to said selected protein in the sample;

(b) removing said support material from the sample, the support carrying therewith the selected protein;

(c) subjecting the removed selected protein to digestion under conditions such as to form therefrom an antigenically distinctive fragment of the said protein; and (d) assaying the said fragment and therefrom determining the amount of said selected protein in the liquid sample.

An example of the procedure is as follows. The serum sample (50 μl) is incubated with an allergen-coated paper disc (Pharmacia Uppsala, Sweden) for 3 hours at room temperature. After three washings with physiological saline, the disc is incubated with 150 μl 0.15N HCl containing 1 mg/ml of pepsin for 5 min at room temperature. The digestion is then stopped by addition of 30 μl of 2M tris (hydroxymethyl) methylamine (hereinafter "TRIS"). An antigenically distinctive pepsin-resistant fragment of IgE is then determined by the latex particle method described above. The results obtained with this pepsin elution procedure as compared with those of the known RAST method in the accompanying FIG. 1, in which:

A = *Phleum pratense*
B = House dust mite (*Dermatoph. pteronyss.*)
C = House dust (Greer)
D = House dust (Hollister-Stier)
E = *Dactylis glomerata*
F = Cat epithelium
G = Dog epithelium
H = Horse epithelium
I = *Plantago lanceolata*
J = *Artemisia vulgaris*
K = *Cladosporium herbarum*
L = *Aspergillus fumigatus*

It will be appreciated that this modified RAST assay is merely one example of a preferred general procedure of the invention for assaying a particular IgE antibody, namely of first separating the IgE of interest from any other IgE present and then enzymatically digesting the IgE and assaying a fragment. Total IgE in a sample may, of course, be assayed according to the invention by simple pepsin digestion followed by assay of a fragment which is distinctive of the total IgE. In both these procedures (assay of a particular IgE and of total IgE), the same antibody can be used, this being an antibody raised against a fragment characteristic of all IgE's. Such an antibody will, of course, bind to the said fragment as formed by digestion of any IgE. In the modified RAST procedure described above, selectivity of the assay is achieved by first separating the IgE of interest from admixture with other IgE. This technique of using only one antibody for all IgE assays is highly preferred since whilst it is (at least in theory) possible to prepare antibodies against a distinctive fragment for each IgE antibody, such active fragments tend also to be characteristic of their source (e.g. of the particular human source from which the fragments were obtained) and thus of no utility in assays of the same IgE from a different human being.

It will be appreciated that the modified RAST procedure is an example of a general technique of the invention for assaying proteins, in which the proteins are first insolubilised by binding to a solid phase, and then the solid phase is contacted with an enzyme to digest the protein, a distinctive fragment being subsequently assayed. Another example of this is the determination of thyroid stimulating hormone (TSH) in neonates (see H. Bickel, R. Guthrie and G. Hammersen, Neonatal Screening for Inborn Errors of Metabolism, Berlin, Springer, 219–228 (1980). Blood samples are collected on filter paper discs, which are then dried and sent to the laboratory. The recovery is facilitated by pepsin digestion of the dried blood sample according to the invention. This procedure of collection of blood on paper disc is becoming increasingly popular in underdeveloped countries when transport of samples can be critical.

Further, determination of proteolytic fragments rather than intact protein molecules can also be useful when the assay has to be applied to biological fluid, e.g. intestinal juice or cellular extracts where proteases are abundant. Another application is the determination of antigens incorporated into cellular membranes, e.g. IgE in basophil membrane; the digestion will facilitate the extraction of the antigens from the membrane.

In the method of the invention, the risk of interference from RF and complement factor, and from other non-specific protein-protein interactions, is very substantially reduced since these proteins are normally subject to digestion by such enzymes as pepsin. Further, when a fragment characteristic of the selected protein under test is assayed, interference from cross-reaction of antibodies is also avoided. For example, it is well known in the prior art that antisera against HGH also cross-react with human placental lactogen (HPL). This type of interference is substantially reduced or avoided by the method of the invention. Another example is FSH and LH (luteinising hormone) which cannot be distinguished by antibodies to either, but which, after pepsin digestion, produce different fragments to which antibodies can be raised which distinguish between the fragments. As an illustration of the effectiveness of the present invention in avoiding non-specific interferences, we have found that in a conventional assay of total IgE, using the F(ab')$_2$ fragments of antibody and using 1M sodium chloride as a chaotropic agent, it was still necessary to dilute the serum ten-fold to reduce interferences to an acceptably low level. However, using the method of the present invention, no dilution of the serum samples was necessary. The assay in both cases was by latex particle method (a) referred to above, and the enzyme used was pepsin.

The method of the invention can provide an increase in the sensitivity of an assay, even when the protein under assay is first destroyed by digestion. The reason for this is as follows. When a protein is injected into an animal the antibodies produced by this animal are directed against a number of antigenic determinants representing various regions of the protein molecule. Some of these determinants are not accessible to antibodies in the intact protein. However, the animal can make antibodies against these hidden determinants because of the in vivo partial digestion of the inoculated protein. In vitro digestion with pepsin or other proteases can reveal the hidden antigenic determinants and, therefore, allow the antibodies directed against these determinants to be now involved in the reaction with, as a result, increase in sensitivity.

As an illustration of this increase in sensitivity, we have found that using the general latex particle assay technique (a) referred to above, the sensitivity of the assay of the present invention is 0.5 to 1.0 IU per ml. whereas using the same assay (but without pepsin digestion) the sensitivity was 5 to 10 IU per ml. The particular procedure used was to mix the IgE-containing sample (50 μl) with 0.15N hydrochloric acid (150 μl) containing 4 mg/ml pepsin. After 5 minutes' incubation at room temperature, the digestion was stopped by addition of 2M tris (hydroxymethyl) methylamine (30 μl). The IgE fragments were then assayed by the latex particle technique (a) described above.

Some errors in prior art immunoassays of proteins are due not to the technique itself but to bad conditions of storage or shipping of the samples. The protein to be assayed can be altered by changes in temperature, and by the proteases present in the samples (e.g. plasmin) or released by contaminating bacteria. A systematic treatment of the samples with a protease such as pepsin, in accordance with the present invention, and the use of a peptide as antigenic traget rather than the whole protein molecule, decreases the risk of error. Peptides usually have a greater resistance to denaturation and further proteolysis than do proteins.

In order that the invention may be more fully understood, the following Examples are given by way of illustration only.

EXAMPLE 1

1. Preparation of antigenically distinctive fragment of IgE

IgE from an IgE-myeloma patient was precipitated with 40% saturated solution of ammonium sulphate and separated on a DEAE Sephadex A-50 column (Pharmacia) using a linear gradient from 0.05 to 0.5M TRIS-HCl buffer, pH 8.0. The IgE was then further purified by chromatography on a 2.5×100 cm column of Ultrogel AcA 4-4 (LKB) in PBS. Possible contamination of the final product (10–15 g/l IgE) was checked for IgG, IgA and IgM by immunonephelometry. Only IgG was detected and that was at a concentration less than 0.5% of total protein.

The IgE was digested in 0.1M acetate buffer, pH 4.5, for 24 hours at 37° C. with crystalline pepsin with an enzymatic protein ratio of 1:50(w/w). The reaction was stopped by raising the pH to 8.0 with solid TRIS, and the mixture filtered on a column 2.5×100 cms of Ultrogel AcA 4-4 in PBS. The column separated the digested mixture into three peaks with molecular sizes >30,000 and five peaks of small peptides. The Fc" fragment, in the third major peak, was chosen as the antigenically distinctive fragment of IgE. This is a known fragment of IgE enzymic digestion. It contains antigenic determinants pertaining to both the F(ab')2 and Fc portions of IgE.

From 50 mg of IgE, about 1.5 mg of Fc" fragment was recovered as estimated by absorption at 280 nm ($E_{1\% \ 1cm}^{280}=18.06$). To avoid aggregation during storage in frozen state, the material was kept at 4° C. in saline containing 4 g/l sodium azide.

The molecular weight of the Fc" fragments at concentrations of 1.5 mg/ml, was estimated at 32,000 daltons.

2. Preparation of antiserum to Fc" fragment

Anti-sera against the Fc" fragments of IgE were raised in 3 New Zealand rabbits by intradermal injection, at multiple sites every two weeks, of 100 μg of Fc" fragment in 500 μl of physiological saline and in 500 μl of complete Freunds' adjuvant. The animals were bled after the third injection. The anti-serum was made specific by passage through an IgG Sepharose immunosorbent column (to remove antibodies not specific to the Fc" fragment).

To test the specificity of the antiserum obtained, double immunodiffusion tests were carried out with both F(ab')2 and Fc fragments of the original IgE. The results showed that the antiserum was exclusively directed against the Fc" fragment. This antiserum is thus superior (for the assay purposes of the invention) to antisera directed against whole IgE, or the Fc or F(ab')2 fragments, or the ε-chain because the specificity is restricted to determinants which are resistant to heat and to the protease used.

The antiserum so made can be used in the method of the invention for the assay of IgE (via the Fc" fragment thereof). However, we describe below the further refinement of preparing the F(ab')2 fragments thereof to use as the "antibody" component in the assay.

3. Preparation of F(ab')2 fragments of antiserum

The antiserum produced in (2) above was treated with ammonium sulphate to precipitate the IgG antibody which was then chromatographed on DEAE cellulose, and then subjected to pepsin digestion in 0.1M acetate buffer, pH 4.5, for 24 hours at 37° C. using an enzyme/protein ratio of 1/50 (w/w). The reaction was stopped by the addition of solid TRIS (to raise the pH to 7.2) and the F(ab')2 fragments produced were recovered by filtration on an Ultrogen AcA 4-4 column in a buffer of 1M sodium chloride with 1/5M phosphate buffer, pH 7.2. After concentration and dialysis into physiological saline, aliquots of 3 to 5 mg/ml of the F(ab')2 fragments were stored at 4° C. in the presence of 4g/liter sodium azide.

4. Latex coated with F(ab')2 fragments

To 100 μl of a 10% (w/v latex (0.8μ) suspension was added a mixture of 300 μl of the F(ab')2 fragments (total weight=1.2 mg) and 800 μl of a 5-fold diluted glycine buffered saline (0.17M glycine in 0.1M NaCl adjusted to pH 9.2 with NaOH and containing 0.4 g/l sodium azide preservative). After 30 minutes' incubation at room temperature, latex was washed once with 2 ml of a 5-fold diluted glycine buffered saline and twice with 2 ml of the buffered saline containing 10 g/l bovine serum albumin (GBS-BSA). After re-suspension in 2 ml GBS-BSA and sonication for 10 seconds the latex was lyophilised and stored at 4° C. in well stoppered bottles. Daily before use, the latex was resuspended in 200 μl of distilled water, diluted with 1.8 ml of GBS-BSA and sonicated for 10 seconds.

When whole IgG is used (rather than the F(ab')2 fragments thereof), it may be coated on latex particles in a generally similar manner.

5. Assay procedure

The assay procedure by PACIA is essentially as follows. The latex (prepared as above, i.e. coated with antiserum or F(ab')2 fragments thereof) is mixed with the sample to be assayed. Some of the latex agglutinates but the remainder does not. The unagglutinated latex is then counted, so giving a measure of the amount of agglutinated latex which, in turn, is indicative of the quantity of IgE fragments in the sample under assay.

In human serum, there will be normal IgE and "antibody IgE" which is responsible for allergic responses. Total IgE may be assayed by subjecting the whole serum to pepsin assay to generate the Fc" fragments (and destroy other serum proteins), which are then assayed with the latex. Alternatively, any selected IgE can be assayed by first selectively extracting it from the serum and then enzymically digesting it to provide Fc" fragments. The selective extraction may conveniently be as described above for RAST, i.e. it may involve the use of an allergen-coated disc which selectively binds with the particular "antibody-IgE" directed against that allergen. The washed disc is then introduced with pepsin to digest the IgE and convert it to Fc" fragments.

In the assay of whole (total) IgE in serum, the serum is first clarified by addition of an approximately equal volume of Freon 113 (Freon is a trade mark), vortexing and centrifugation for 5 mins. at 5000 revs/min. Aliquots of about 100 μl of the clear supernatant are then incubated for 10 min. at 37° C. with 300 μl of HCl-pepsin (0.15 mol/l HCl plus 4 g/l twice recrystallised pepsin). Digestion is stopped by addition of 20 μl of 2 mol/l TRIS. The mixture so formed is then assayed using the latex particles.

EXAMPLE 2

TSH assay using pepsin treatment of samples

Principle:

Carboxylated latex particles are covalently coated with proteins of human pituitary extract which contains TSH. Agglutination is caused by a mixture of rabbit anti-TSH antibodies and human rheumatoid factor (RF) as agglutinator. Agglutination is inhibited by TSH to be determined. Pepsin treatment of samples destroys serum interferences. The enzyme digestion conditions are such that the TSH remains immunologically reactive, i.e. it is substantially unaffected by the digestion.

Assay:

Sample treatment: 10 μl of sample is phosphate buffered saline (PBS) containing 7% bovine serum albumin (BSA) is mixed with 100 μl of 0.15N HCl containing 5 mg pepsin/ml; incubation time=10 min at room temperature.

100 μl of 0.3% $Na_2HPO_4$ containing 18% polyethylene glycol (PEG) 6000 is added to stop the pepsin digestion.

30 μl of treated sample is mixed sequentially with 30 μl of rabbit anti-TSH (diluted in PBS-0.1% BSA), 30 μl of human RF (diluted in PBS-0.1% BSA) and 30 μl of latex particles (suspended in PBS-0.1% BSA).

Incubation time: 25 min at 37° C. The sensitivity of this system is 0.1 ng TSH/ml.

We claim:

1. A method of immunoassay of a selected protein in a liquid sample also containing one or more other non-selected proteins, which comprises reducing or avoiding interference from said other proteins by mixing with the liquid sample a protein-digesting reagent, and allowing protein digestion to occur under conditions such that the said selected protein provides, in the resulting mixture, a fragment which is distinctive only of said selected protein in the said mixture; and thereafter assaying the said distinctive fragment by reaction with an antibody raised against said distinctive fragment and determining therefrom the amount of said selected protein present in said liquid sample.

2. A method according to claim 1, wherein the said reagent is an enzyme and said selected protein is broken down by said enzyme to form said distinctive fragment.

3. A method according to claim 2, wherein the said distinctive fragment is assayed by reacting it with the F(ab) region of an antibody raised against the said distinctive fragment.

4. A method according to claim 2, wherein said distinctive fragment is assayed by reacting it with whole antibody.

5. A method according to claim 2, wherein distinctive fragment is assayed by reacting it with F(ab')$_2$ fragments of an antibody.

6. A method according to claim 1, wherein said distinctive fragment is assayed by a particle agglutination technique in which the amount of said selected protein is determined from the extent of agglutination of finely divided particles.

7. A method according to claim 1, wherein said liquid sample is a biological fluid.

8. A method according to claim 1, wherein said protein-digesting agent is an enzyme selected from pepsin, papin and trypsin.

9. A method of assaying a selected protein in a biological fluid sample also containing one or more other non-selected proteins, whereby interference in the assay from said other proteins is avoided and the specificity and accuracy of the assay improved, which method comprises:
(a) contacting said sample with an inert solid support material bearing a reagent which selectively binds only to said selected protein in said sample;
(b) removing said support material from said sample, said support material carrying therewith said selected protein;
(c) subjecting the removed selected protein to digestion under conditions such as to form therefrom an antigenically distinctive fragment of the said protein; and
(d) assaying the said distinctive fragment by reaction with an antibody raised against said distinctive fragment and therefrom determining the amount of said selected protein in said liquid sample.

10. A method according to claim 9, wherein said selected protein is a particular IgE antibody and the said other proteins include at least one other IgE which is incapable of binding to the reagent on said inert solid support material.

11. A method according to claim 10, wherein the said inert solid support material is a sheet of material bearing an allergen against which the particular IgE is directed.

12. A method according to claim 9, wherein in step (d), said distinctive fragment is assayed by reaction with the F(ab) region of an antibody reactive therewith, and wherein said distinctive fragment is assayed by a particle agglutination technique.

13. A method according to claim 12, wherein said distinctive fragment is assayed by reaction with whole antibody.

14. A method according to claim 12, wherein said distinctive fragment is assayed by reaction with F(ab')$_2$ fragments of an antibody.

15. A method according to claim 9, wherein in step (c) the digestion is effected by an enzyme.

16. A method of assaying a selected protein in a liquid sample also containing one or more other non-selected proteins, whereby interference from said other proteins is reduced or avoided, which comprises the steps of:
(a) preliminarily subjecting samples of said selected protein to enzymatic digestion under varying conditions, separating the protein fractions produced and determining the conditions of digestion which result in production of an antigenically distinctive fragment of said selected protein; and thereafter:
(b) subjecting said liquid sample to enzymatic digestion utilising said conditions of digestion dtermined in step (a);
(c) stopping said digestion; and
(d) assaying the resulting mixture to determine therein the amount of said antigenically distinctive fragment of said selected protein by reaction, and therefrom determining the amount of said protein in the liquid sample.

17. A method according to claim 16, wherein said liquid sample is human serum; said enzyme is pepsin; and wherein in step (d) said antigenically distinctive fragment is assayed by reaction thereof with the F(ab) region of an antibody raised against said antigenically distinct fragment, in the presence of finely divided particles, the amount of said antigenically distinct fragment being determined by measurement of the extent of agglutination of the said particles.

18. A method according to claim 17, wherein said antigenically distinct fragment is assayed by reaction with whole antibody raised against said antigenically distinct fragment.

19. A method according to claim 17, wherein said antigenically distinct fragment is assayed by reaction with F(ab')$_2$ fragments of the antibody raised against said antigenically distinct fragment.

* * * * *